(12) United States Patent
Kurzweil et al.

(10) Patent No.: US 9,456,762 B2
(45) Date of Patent: Oct. 4, 2016

(54) ATRIAL FIBRILLATION DETECTION AND ASSOCIATED METHODS

(71) Applicant: Medicomp, Inc., Melbourne, FL (US)

(72) Inventors: Raymond C. Kurzweil, Newton, MA (US); Lucy Gibson, Belmont, MA (US); Paul Albrecht, Bedford, MA (US); Paul Grimshaw, Acton, MA (US)

(73) Assignee: Medicomp, Inc., Melbourne, FL (US)

( * ) Notice: Subject to any disclaimer, the term of this patent is extended or adjusted under 35 U.S.C. 154(b) by 0 days.

(21) Appl. No.: 14/835,091

(22) Filed: Aug. 25, 2015

(65) Prior Publication Data

US 2015/0359449 A1 Dec. 17, 2015

Related U.S. Application Data

(63) Continuation of application No. 13/867,804, filed on Apr. 22, 2013, now Pat. No. 9,131,867, which is a continuation of application No. 12/564,271, filed on Sep. 22, 2009, now Pat. No. 8,428,705, which is a continuation of application No. 11/074,320, filed on Mar. 7, 2005, now Pat. No. 7,596,405.

(51) Int. Cl.
| | |
|---|---|
| A61B 5/046 | (2006.01) |
| A61B 5/02 | (2006.01) |
| A61B 5/0452 | (2006.01) |
| A61B 5/00 | (2006.01) |

(52) U.S. Cl.
CPC .......... *A61B 5/046* (2013.01); *A61B 5/02028* (2013.01); *A61B 5/04525* (2013.01); *A61B 5/7271* (2013.01); *A61B 5/746* (2013.01); *A61B 5/7445* (2013.01)

(58) Field of Classification Search
CPC .................................................. A61B 5/046
See application file for complete search history.

(56) References Cited

U.S. PATENT DOCUMENTS

| | | | |
|---|---|---|---|
| 4,721,114 A | 1/1988 | DuFault et al. | |
| 4,793,361 A | 12/1988 | DuFault | |
| 5,778,881 A | 7/1998 | Sun et al. | |
| 6,035,231 A | 3/2000 | Sornmo et al. | |
| 6,041,251 A | 3/2000 | Kim et al. | |
| 6,411,840 B1 | 6/2002 | Bardy | |
| 6,490,479 B2 * | 12/2002 | Bock ................. | A61B 5/02405 600/512 |
| 6,597,943 B2 | 7/2003 | Taha et al. | |
| 6,615,075 B2 | 9/2003 | Mlynash et al. | |
| 6,701,183 B2 | 3/2004 | Baker et al. | |
| 6,704,595 B2 | 3/2004 | Bardy | |

(Continued)

OTHER PUBLICATIONS

Detection of Atrial Persistent Rhythm Based on P-wave Recognition and RR Interval Variability, Zurro et al., Computers in Cardiology, 1995 IEEE, pp. 185-188.

(Continued)

*Primary Examiner* — Amanda Patton
(74) *Attorney, Agent, or Firm* — Mark Malek; Kelly G. Swartz; Widerman Malek PL

(57) ABSTRACT

A method to detect atrial fibrillation including the steps of receiving an electrical signal representative of a beating heart, measuring atrial activity over a time window of three or more beats, measuring beat interval variation over the time window, combining the measures of atrial activity and beat interval variation to produce an indication of an atrial fibrillation condition in the electrical signal, and generating an alert based on the indication of an atrial fibrillation condition.

9 Claims, 10 Drawing Sheets

(56) References Cited

U.S. PATENT DOCUMENTS

| | | | |
|---|---|---|---|
| 7,187,965 B2 | 3/2007 | Bischoff et al. | |
| 7,194,300 B2 | 3/2007 | Korzinov | |
| 7,212,849 B2* | 5/2007 | Zhang | A61N 1/3622 |
| | | | 600/509 |
| 7,596,405 B2 | 9/2009 | Kurzweil et al. | |
| 8,428,705 B2 | 4/2013 | Kurzweil et al. | |
| 9,131,867 B2 | 9/2015 | Kurzweil et al. | |
| 2006/0084883 A1* | 4/2006 | Linker | A61B 5/02405 |
| | | | 600/518 |

OTHER PUBLICATIONS

A New Method for Detecting Atrial Fibrillation Using R-R Intervals, Moody et al., Computers in Cardiology, 1983 IEEE, pp. 227-230.

Analysis of the Dynamics of RR Interval Series for the Detection of Atrial Fibrillation Episodes, Computers in Cardiology, 1997 IEEE, vol. 24, pp. 77-80.

Automatic detection of atrial fibrillation using the coefficient of variation and density histograms of RR and RR intervals, Medical & Biological Engineering & Computing 2001, vol. 39, pp. 664-671.

Atrial Activity Enhancement by Wiener Filtering Using an Artificial Neural Network, IEEE Transactions on Biomedical Engineering, vol. 48, No. 8, Aug. 2001, pp. 940-944.

Automated Assessment of Atrial Fibrillation, Computers in Cardiology, 2001 IEEE, pp. 117-120.

Principal component analysis and cluster analysis for measuring the local organization of human atrial fibrillation, Medical & Biological Engineering & Computing 2001, vol. 39, pp. 656-663.

Recurrent Patterns of Atrial Depolarization During Atrial Fibrillation Assessed by Recurrence Plot Quantification, Censi et al., Annals of Biomedical Engineering, vol. 28, 2000, pp. 61-70.

Frequency Analysis of Atrial Fibrillation, Langley et al., Computers in Cardiology, IEEE 2000, vol. 27, pp. 65-68.

Comparison of Bivariate and Contextual Analysis in Discrimination of Atrial Fibrillation from Surface Electrocardiogram, Shahane et al., Computers in Cardiology, 1996 IEEE, pp. 441-444.

Automatic Detection of Atrial Fibrillation and Flutter Using the Differentiated ECG Signal, Giraldo et al., Computers in Cardiology, 1995 IEEE, pp. 369-372.

Validation of an Algorithm for Atrial Fibrillation and Flutter Diagnosis, Giraldo et al., Computers in Cardiology, 1997 IEEE, vol. 24, pp. 485-488.

Detecting Atrial Fibrillation Using Spatial Precision, Schoenwald et al., IEEE Engineering in Medicine and Biology, May/Jun. 1996, pp. 45-51.

Detection of Spontaneous Termination of Atrial Fibrillation, Logan et al., IEEE Computers in Cardiology, Sep. 19-22, 2004, pp. 1-8.

Automatic P-wave analysis of patients prone to atrial fibrillation, Clavier et al., Medical & Biological Engineering & Computing 2002, vol. 40, pp. 63-71.

Spatiotemporal QRST cancellation techniques for atrial fibrillation analysis in the surface ECG, Stridh et al., Signal Processing Report SPR-44, Jun. 8, 1998, pp. 1-29.

Spatiotemporal QRST cancellation techniques for improved characterization of atrial fibrillation in the surface ECG, Stridh et al., Signal Processing Report SPR-44, Jun. 8, 1998, pp. 1-3.

P-Wave Trending: A Valuable Tool for Documenting Supraventricular Arrhythmias and Av-Conduction Disturbances, J. de Bie, 1991 IEEE, pp. 511-514.

Detection of Atrial Fibrillation Using Artificial Neural Networks, Artis et al., 1992 IEEE, pp. 173-176.

Discrimination of Atrial Arrhythmias using Autoregressive Modelling, Bloem et al., 1992 IEEE, pp. 235-238.

A New Algorithm for Measuring Atrial Fibrillation Organization, Sih et al., Computers in Cardiology, 1998 IEEE, vol. 25, pp. 273-276.

A Computer Package Generating Non-Invasive Atrial Electrograms: Detection and Subtraction of QRS and T Waves, Hnatkova et al., Computers in Cardiology, 1998 IEEE, vol. 25, pp. 533-536.

Atrial Activity Extraction Based on Blind Source Separation as an Alternative to QRST Cancellation for Atrial Fibrillation Analysis, Computers in Cardiology, 2000 IEEE, vol. 27, pp. 69-72.

Stedman's Medical Dictionary; Thomas Lathrop 1853-1938 Stedman; 28th Edition; Baltimore, Md. Lippincott Williams & Wilkins 2006, p. 001, to show the definitions of "PR interval" and "R-R Interval" (1 page).

USPTO's Interview Summary dated Sep. 15, 2014 in related U.S. Appl. No. 13/867,804 (3 pages).

USPTO's Non-Final Office Action dated May 7, 2012 in related U.S. Appl. No. 12/564,271 (11 pages).

USPTO's Interview Summary dated Dec. 24, 2012 in related U.S. Appl. No. 12/564,271 (11 pages).

USPTO's Non-Final Office Action dated May 22, 2008 in related U.S. Appl. No. 11/074,320 (12 pages).

USPTO's Interview Summary dated Jun. 18, 2008 in related U.S. Appl. No. 11/074,320 (12 pages).

* cited by examiner

ATRIAL FIBRILLATION DETECTION AND ASSOCIATED METHODS

RELATED APPLICATIONS

This application is a continuation of U.S. patent application Ser. No. 13/867,804 filed on Apr. 22, 2013 and titled Atrial Fibrillation Detection which, in turn, is a continuation of U.S. patent application Ser. No. 12/564,271, now U.S. Pat. No. 8,428,705 filed on Sep. 22, 2009 and titled Atrial Fibrillation Detection, and a continuation of U.S. patent application Ser. No. 11/074,320, now U.S. Pat. No. 7,596,405 filed on Mar. 7, 2005, and titled Atrial Fibrillation Detection, the contents of each of which are incorporated herein by reference in their entireties.

BACKGROUND

Atrial fibrillation is a cardiac disorder where the heart's two small upper chambers (the atria) quiver instead of beating effectively. With atrial fibrillation, blood may not be pumped completely out of the atria, so that the blood may pool along the atrial walls, and eventually clot. If a blood clot in the atria leaves the heart and becomes lodged in an artery in the brain, a stroke may result.

Treatments for atrial fibrillation (AFib) include medications to decrease blood clotting, medications to slow down rapid heart rate associated with AFib and electric shock to restore normal heart rhythm when medications do not improve symptoms. Other techniques include surgery to disrupt electrical pathways that generate AFib and uses of atrial pacemakers to regulate the heart rhythm.

The heart beat has two main phases called "diastole" where the heart relaxes and fills with blood and "systole" where the heart contracts and pumps out the blood. The contraction of the heart muscle is caused by an electrical wavefront that typically starts in the so called "sinoatrial" (SA) node of the atrium and spreads over the two atria. The wavefront reaches the so called "atrioventricular" (AV) node. The AV node delays the signal to allow the atria to finish contracting in response to the electrical activation. The contraction of the atria helps move the blood from the atria to the ventricles.

From the AV node, the electrical signal spreads through the His-Purkinje system, fibers that form a specialized conduction system that quickly propagates the wavefront to all the regions of the ventricles, and causes the ventricles to activate and contract. The contraction of the ventricles pumps the blood into the lungs and the body. At the end of the cycle, the ventricles relax and the whole process repeats.

An electrocardiogram (ECG) is used to assess rhythm disturbances in the heart. The ECG measures electrical activity of the heart as reflected through electrical potentials produced at the body surface. In a medical setting, e.g., doctor's office or hospital, a standard ECG is obtained by placing 10 small electrodes on the patient's body in a specific pattern and recording 12 channels of ECG for a brief period of time. For longer-term ECG monitoring, 3 to 5 electrodes are typically used to obtain 1 or 2 channels of ECG signals.

The ECG signal typically is a repeating pattern of three relatively distinct waveform components. One component is the "P wave" which represents atrial depolarization, e.g., the wavefront generated as the electrical impulse from the sinoatrial (SA) node spreads throughout the atrial musculature. The P wave precedes a second component, the "QRS complex." A "PR Interval" represents the time it takes an impulse to travel from the atria through the AV node, bundle of His, and bundle branches to the Purkinje's fibers. The PR Interval extends from the beginning of the P wave to the beginning of the QRS complex. The "QRS Complex" component represents ventricular depolarization. The QRS complex is a large waveform typically composed of three (3) waves, the Q wave, the R wave, and the S wave. The Q wave is at the beginning of the QRS complex. The Q wave may or may not always be present. The R wave is typically the first positive deflection and the S wave is the negative deflection that follows the R wave. The third component is the "T wave," which represents the electrical recovery of the ventricles (the electrical recovery of the atria is usually buried in the QRS complex or T wave, or is too small to be seen). The time interval between two consecutive beats, the so-called beat interval, is often measured from R-wave of one beat to R-wave of the following beat. The measure between two consecutive R waves is called the RR interval.

The QRS complex is usually the dominant feature of an ECG. The P wave is much smaller than the QRS complex because the atria generate less electrical activity than the much more massive ventricles. Other components of an ECG include the "Q-T Interval" which represents the time necessary for ventricular depolarization and repolarization and extends from the beginning of the QRS complex to the end of a "T wave." By analyzing the pattern of the ECG, medical professionals can gain insight into the condition of the heart.

In an ECG from a healthy heart with normal rhythm, with a non-noisy signal, the large QRS complexes are separated by a fairly flat signal, except for a small upright bump (the P wave) about 120-200 ms before the QRS complex. A P wave is "conducted" when the atrial electrical activity conducts through the AV node, causing electrical activation of the ventricles and the QRS complex. A P wave is considered "non-conducted" when it fails to lead to a QRS complex. Non-conducted P waves can occur because the P wave was premature, or because of the condition called AV block, or other reasons. P waves that are blocked due to AV block are said to be "blocked P waves". By definition, at most one of the P waves in the RR interval is conducted and any other P waves in the same RR interval are non-conducted.

In atrial flutter, the atrial rhythm increases to approximately 250-350 beats per minute. The accelerated atrial rhythm is sometimes visible as continuous waves in the ECG, with several waves appearing in a continuous connected pattern in each RR interval, quite different from the normal pattern of a single P wave in each RR interval. These waves of continuous, cyclic atrial activity are called flutter waves or F-waves, and may form a sawtooth pattern. During atrial flutter, the ventricular response sometimes becomes locked into a regular pattern with the atrial activity, so that for example, every third flutter wave results in a QRS while the other flutter waves are not conducted. In other cases, conduction of the flutter waves is more random, resulting in an irregular ventricular rhythm.

As the rate increases over 350-400 beats per minute, the rapid atrial rhythm is called atrial fibrillation. Sometimes the atrial activity may be visible in the RR interval as continuous, cyclic activity referred to as "f waves," or coarse atrial fibrillation. Typically, the "f waves" are cyclic, but not as organized or consistent in shape as the "F waves" of atrial flutter. When viewed in two ECG channels, the cyclic activity of the "f waves" may be seen to alternate back and forth between channels in what appears to be modulated electrical activity.

At other times, atrial fibrillation may be present with no obvious cyclic activity visible in the ECG, but with low amplitude disorganized "noise" in the baseline. In other cases, there may be total absence of atrial activity, suggesting that the fibrillation has become greatly disorganized.

SUMMARY

Because of the high atrial rate and disorganized atrial activity, atrial fibrillation results in a highly irregular ventricular rhythm. Many AFib detection algorithms use irregular ventricular activity as the sole criterion, although it does not necessarily mean that atrial fibrillation is present. An irregular ventricular rhythm can be caused by another condition besides AFib, such as sinus arrhythmia or atrial premature beats. A more direct indication of AFib or atrial flutter is the presence of certain atrial activity and the near absence of normal P waves. However, normal P waves are much harder to detect than QRS complexes because they are much smaller.

With the above in mind, the present invention is directed to a method of detecting atrial fibrillation (AFib). The method may include receiving electrical signals representative of a beating heart and measuring atrial activity over a time window of three or more beats. The method may also include measuring beat interval variation over the time window, combining the measures of atrial activity and beat interval variation to produce an indication of an atrial fibrillation condition in the electrical signal, and producing the indication with a processing system. Measuring atrial activity may include measuring P waves, and wherein measuring P waves may include analyzing a standard deviation of a PR interval.

The P wave may be classified as conducted when the standard deviation is low. Further, the classification of a PR interval as an irregular rhythm other than AFib depends on the number of P waves detected in that interval classified as conducting. A hysteresis filter may be utilized to increase the reliability of the count of P waves. The electrical signals may be provided from plural electrical channels. The method may also include determining whether one or more P waves are detected during a TQ interval on a channel from the plural channels with a largest expected P-wave, combining a number and times of detected P waves from that channel when plural P-waves are detected; otherwise, and combining a number and times of detected P waves from an alternate one of the plural channels.

Measuring atrial activity may also include computing a measure of the fraction of beat intervals that have one detected P wave. Measuring atrial activity may also include determining if more than one P wave was present in a beat interval, and using information from more than one signal channel representative of a beating heart to detect and classify the P waves. Measuring atrial activity may be for a plurality of channels and may include determining a quality indicator for the measured channels. One of the measures may be selected from the channels based at least in part on the determined quality indicators for the measured channels. Measuring atrial activity may also be performed over the time window and may include producing two or more atrial activity measures in the time window, and combining the atrial activity measures into a representative atrial activity measure for the time window.

The present invention may also include a computer program product residing on a computer readable medium for detecting the presence of atrial fibrillation in an electrical signal. The computer program product may include instructions for causing a computer to receive the electrical signal representative of a beating heart and measure atrial activity over a time window of three or more beats. The computer program product may also include instructions for causing the computer to measure beat interval variation over the time window, combine the measures of atrial activity and beat interval variation to produce an indication of an atrial fibrillation condition in the electrical signal, and produce the indication. Instructions for causing a computer to measure atrial activity may include instructions for causing a computer to measure P waves. The instructions for measuring P waves may cause a computer to analyzing a standard deviation of a PR interval.

DETAILED DESCRIPTION

Figure 1:
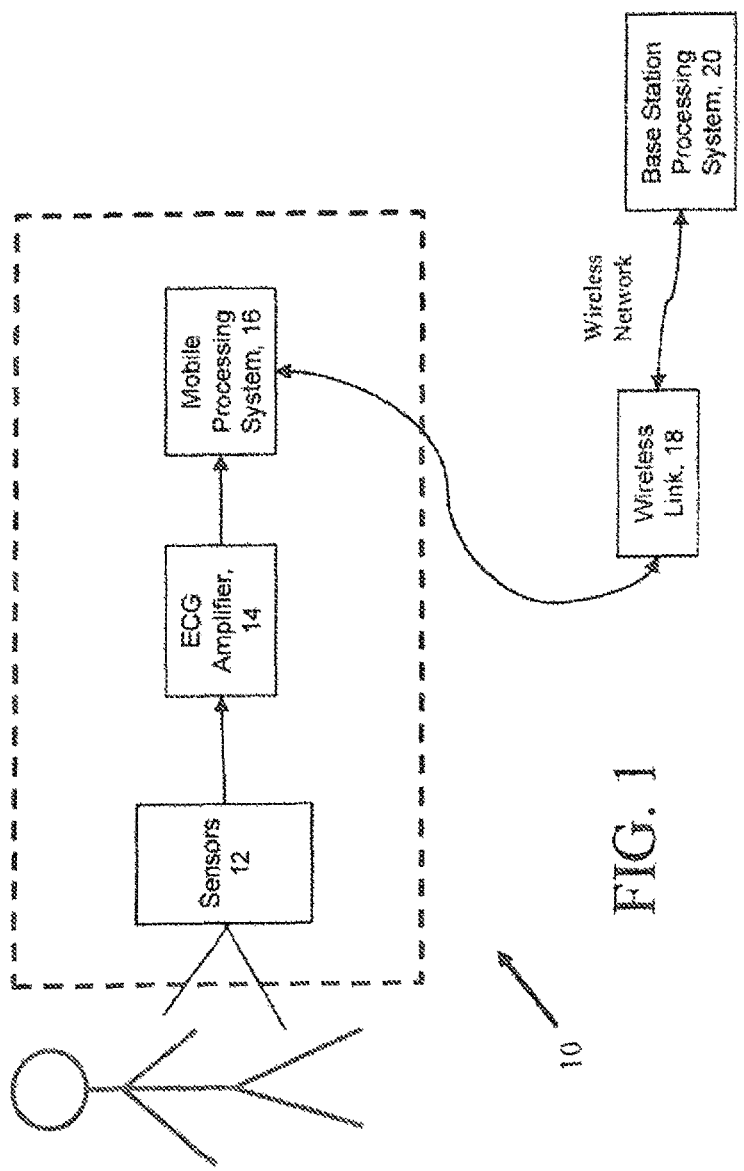
FIGS. 1-3 are block diagrams of hardware used to monitor cardiac activity in a user.

Referring to FIG. 1, a patient monitor device 10 ("monitor") includes for instance, sensors 12, an amplifier 14 and mobile processing system 16 to process signals and a communication link 18, e.g., a wireless link to wirelessly transmit results of processing to a remote computer system ("base station") 20. The communication link 18 between the base station 20 and monitor 10 is bi-directional and may involve data and control. In one embodiment, the monitor 10 receives data from an ECG to detect signal patterns that indicate cardiac abnormalities. The amplifier 14 amplifies the ECG signal and filters it to preserve frequencies in the range of, e.g., 0.05 to 100 Hz or so. The amplifier 14 feeds the signal to an ND converter (not shown) that digitizes the signal, typically at a sample rate in the range of 250 to 360 samples per second. The digitized signal, e.g., the digitized ECG, is transferred to the processing system 16 where the digitized ECG is processed.

Figure 2:
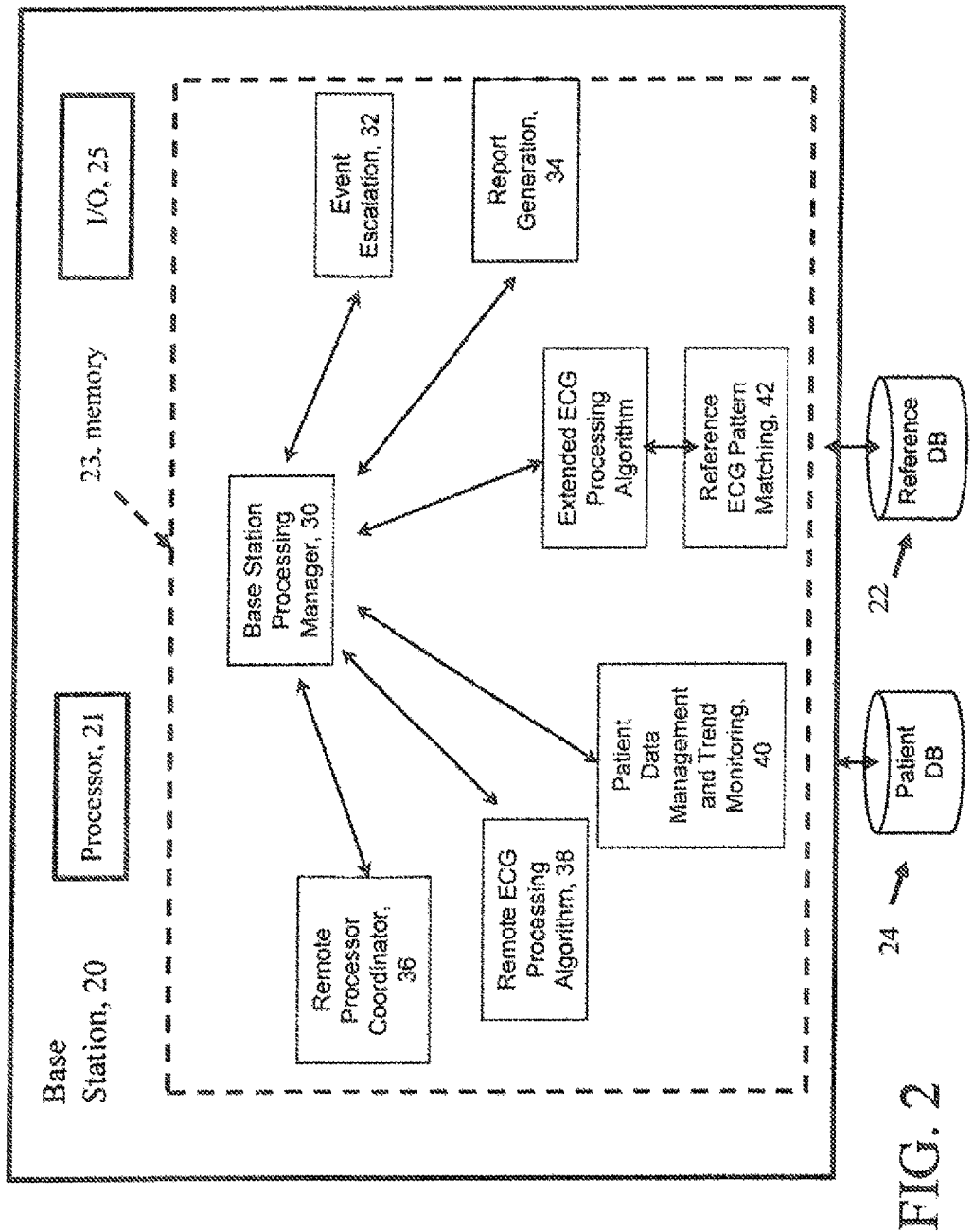

Referring to FIG. 2, the base station 20 may maintain a large database 22 of physiologic signals. The database 22 is stored in a form that allows the physiologic signals to be used as reference templates for beat and rhythm classification by the patient monitor device 10 or base station 20. The base station 20 can maintain a historical reference data on the subject 24, including ECG data, templates and reference data. The base station 20 includes a processor 21, memory 23 and I/O device(s) 25. The base station executes a Base Station Processing Manager 30, Event Escalation process 32, Algorithm Report Generation 34, a Remote Processor Coordinator process 36, a Remote ECG Processing Algorithm 38, Patient Data Management and Trend Monitoring 40 that maintains database 24 and reference ECG Pattern Matching 42, that maintains database 22 and extended ECG processing.

Figure 3:
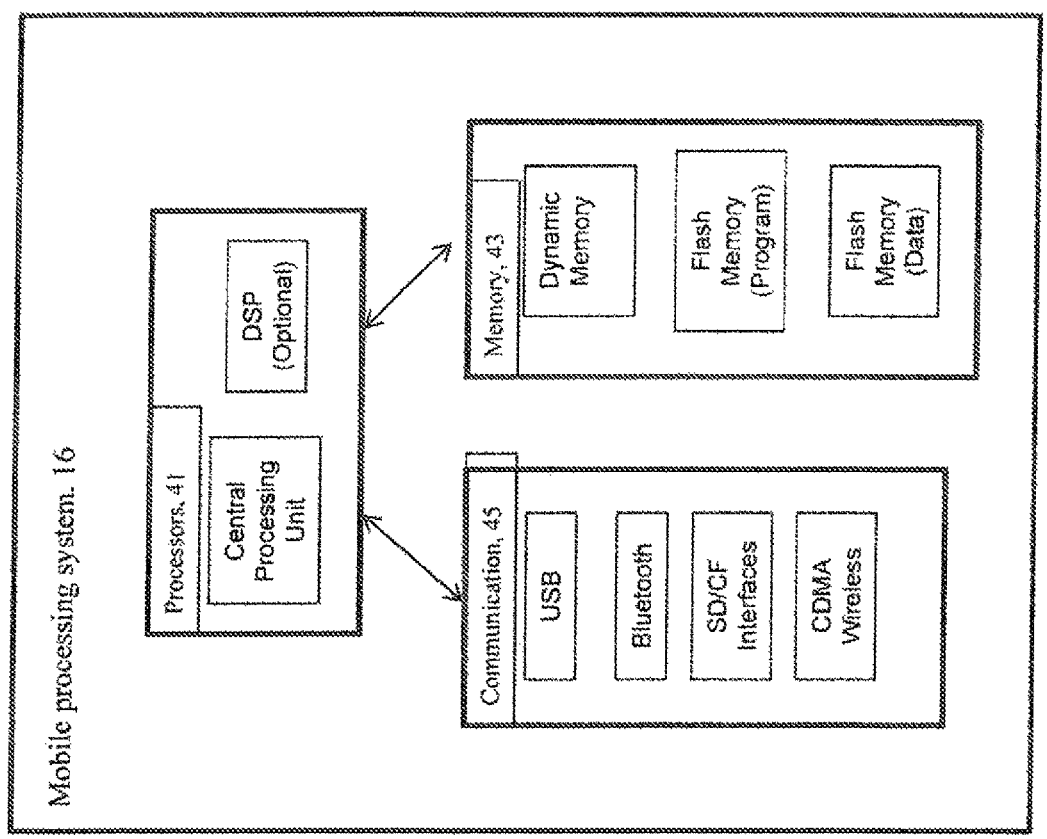

Referring to FIG. 3, the mobile processing system 16 of the patient monitor 10 can be networked and operate in conjunction with the base station 20 (FIG. 1). The mobile processing system 16 includes a central processing unit (CPU) and/or a digital signal processor (DSP) 41 to process and/or pre-process signals from the patient in order to reduce the amount of data sent to the base station 20. In addition, the mobile processing system 16 includes memory 43 and a communications module 45 to communicate with the base station 20. The monitor 10 can also include user interface devices, e.g., keyboard or keypad, a display, etc. not shown.

The role of the base station 20 when used with the monitor 10 is to receive data from the monitor 10, verify results from the monitor 10, and initiate appropriate actions if warranted by the results. If a result is verified, the action may include sending alerts, notifications to the user and so forth. If the result is not verified, the base station 20 may communicate with the monitor 10 to modify the monitor's 10 processing. The base station may improve detection of episodes that are likely to be important while minimizing false negatives.

In one embodiment, processing workload is split between the mobile device 10 and base station 20 using the Base Station Processing Manager 30 and Remote Processor Coordinator process 36. The balance of workload can be adjusted to suit available mobile technology processing ability. In some embodiments, the mobile processor 16 is a pre-processor for the base station 20, whereas in other embodiments the mobile processor 16 executes an algorithm configured with operating parameters and reference data and operates in standalone mode. The mobile processor 16 can save exemplary events and information in non-volatile memory or upload the events and information to the base station 20.

Typically, in operation, the monitor 10 is not in constant communication with the base station 20. Rather, the monitor 10 sends periodic updates of information. Immediate contact with the base station 20 occurs only if there is a potentially serious event, or an event that needs additional processing resources of the base station 20.

The base station 20 can be a single computer at a user's home or can be part of a larger facility, e.g., a server farm. The base station may maintain 24 a detailed record of ECG findings over time for the patient. A base station may be configured to escalate specific types of findings by sending data to a base station at a clinical monitoring facility, or by generating a fax. A single base station may be capable of concurrently servicing more than one patient monitor 10. The base station 20 at a monitoring facility may establish a session with the monitor 10 so that the same server continues to interact with the monitor 10. A base station 20 at the monitoring facility may be coordinated with a patient medical record. A base station 20 at a monitoring facility may be configurable on a per-patient basis to specify escalation rules for different types of findings.

The base station 20 can have access to any of the data in the monitor 10. In addition, the base station 20 may send updated parameters that determine the general operation of the monitor 10, including the types of episodes that are detected and reported. The base station 20 can send corrections to internal classifications or templates produced and held by monitor 10. Reference data can include ECG beat templates, including historical data for the patient, e.g. what is normal for that patient, and instructions intended for the user.

Figure 4:
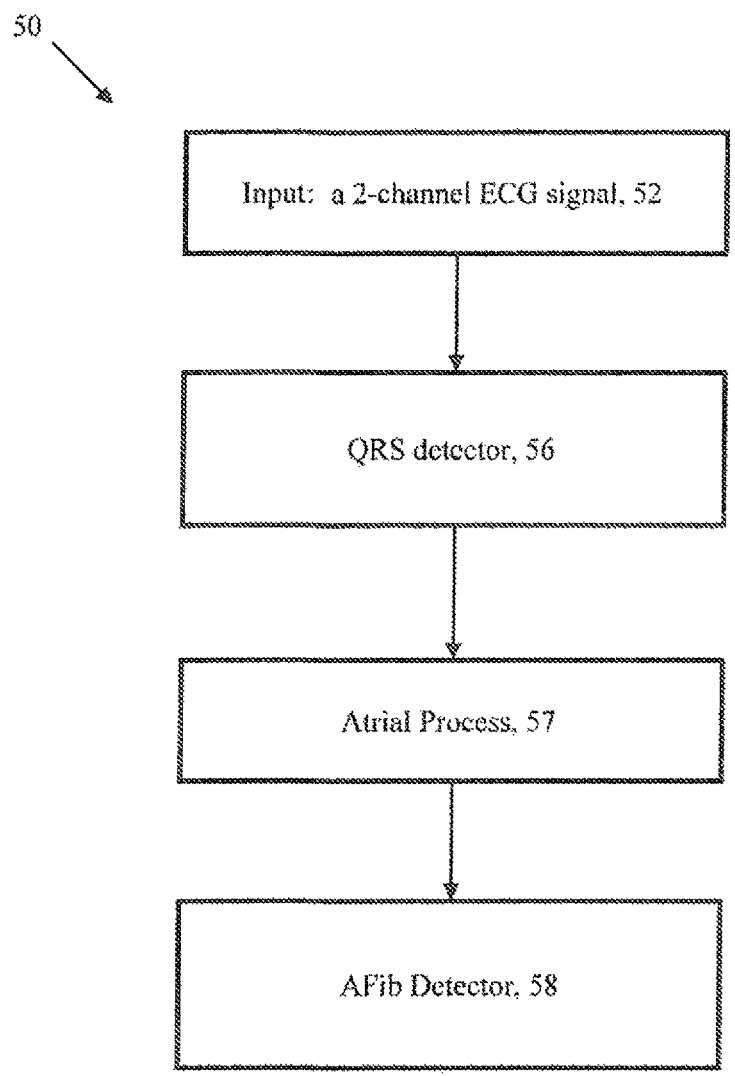
FIGS. 4-10 are flow charts depicting aspects of atrial fibrillation detection.

Referring to FIG. 4, an atrial fibrillation (AFib) detection 50 process is shown. A two-channel ECG signal 52 is input. The QRS detector 56 determines the time and type of each QRS complex in the ECG signal. The time of the QRS complex is typically given as the peak of the R wave, but other reference points could be used, such as the QRS onset. The atrial process 57 determines the atrial activity in the ECG. The atrial activity measure is based on the detection of P waves. Other measures of atrial activity are described below.

The AFib detector 58 takes input from the atrial process 57 and the QRS detector 56 (via the atrial process) and makes a determination of AFib for a time window. The time window is typically a specified duration or a specified number of beats. For one example the time window is 121 beat intervals and the determination of atrial fibrillation is associated with a beat in the middle of the time window.

The AFib detector produces an indication of atrial fibrillation for a time window in the signal. Typically, the indication is produced for successive time windows, which may or may not overlap. The AFib indication is computed by combining atrial activity measures with beat interval variation measures. Typically, each measure is associated with one of the beats in the time window. For measures that are produced from data spanning more than one beat interval, the measure is typically associated with the middle or last (most recent) beat.

Figure 5:
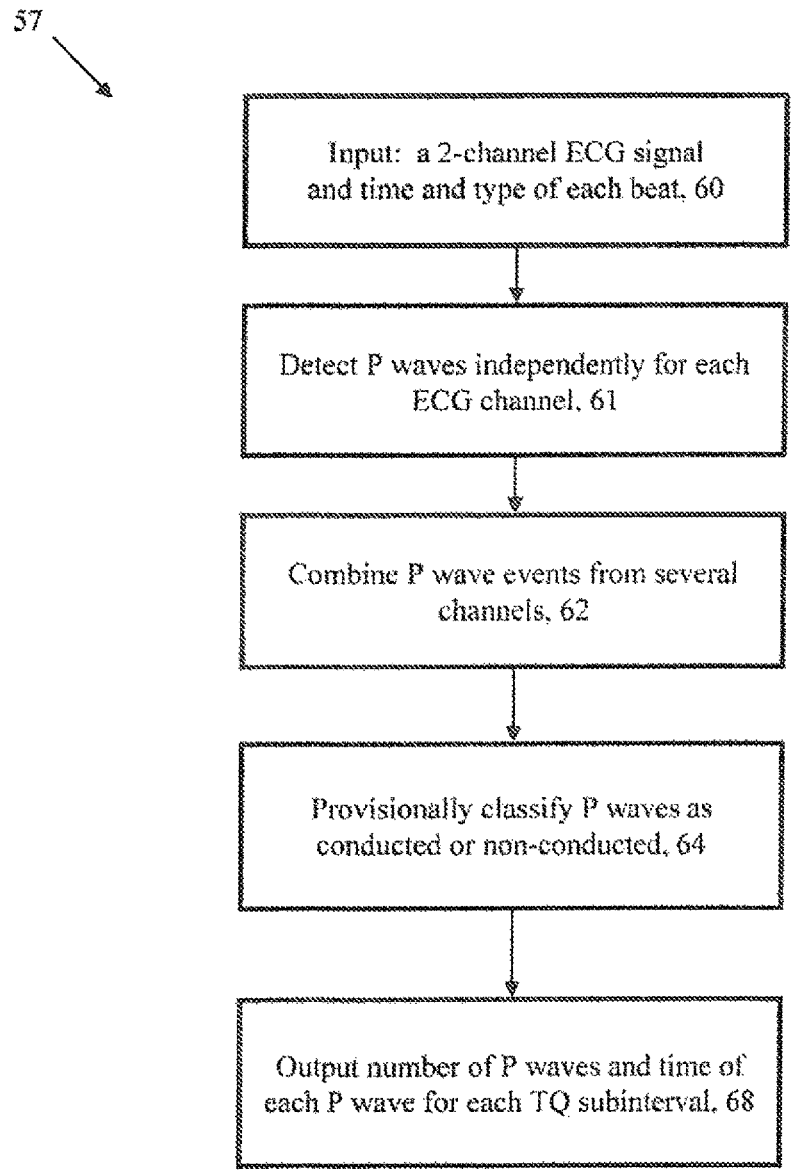

Referring to FIG. 5, the atrial process 57 receives as input 60 a raw 2-channel ECG signal and the time and type of each beat. The atrial process 57 is updated each time a QRS event is detected in the ECG signal. The atrial process 57 detects the presence of P waves 61 at specific times within the TQ interval defined by the offset of the T wave and the onset of the following QRS interval. More than one P wave can be detected in a TQ interval. The atrial process 57 outputs 68 P-wave events for each TQ interval, e.g., the number and times of detected P wave events. For each TQ interval, the atrial process 57 combines 62 the P-wave event data from both channels into atrial activity measures using the following rules:

If one or more P-waves are detected on the primary P-wave channel (channel with largest expected P-waves), the combining process 62 uses the number and times of detected P-waves from that channel. Otherwise, the combining process 62 will use the number and times of detected P-waves from the alternate channel.

The detected P-waves are provisionally classified as conducted or non-conducted 64 based on the following rules: The P wave closest to the R-wave is classified as conducted if 120 ms<PR<400 ms, otherwise it is classified as non-conducted. Other P waves in the same TQ interval are classified as non-conducted. Other modules of the monitor 10 may reclassify the provisionally classified P-waves. The resulting atrial activity measures and the single channel events from the primary channel are made available to other modules of the monitor.

An implementation of the atrial process 57 uses a management layer and two single-channel P-wave processes that implement a P-wave detection algorithm. The P-wave detectors 61 are independent P-wave process instances, one for each channel of ECG. Each independent P-wave detector implements a P-wave detection algorithm. The Management Layer manages the initialization and setup of the P-wave processors. The Management Layer also sends QRS event data to the P-wave processors, and receives back P-wave event data.

Figure 6:
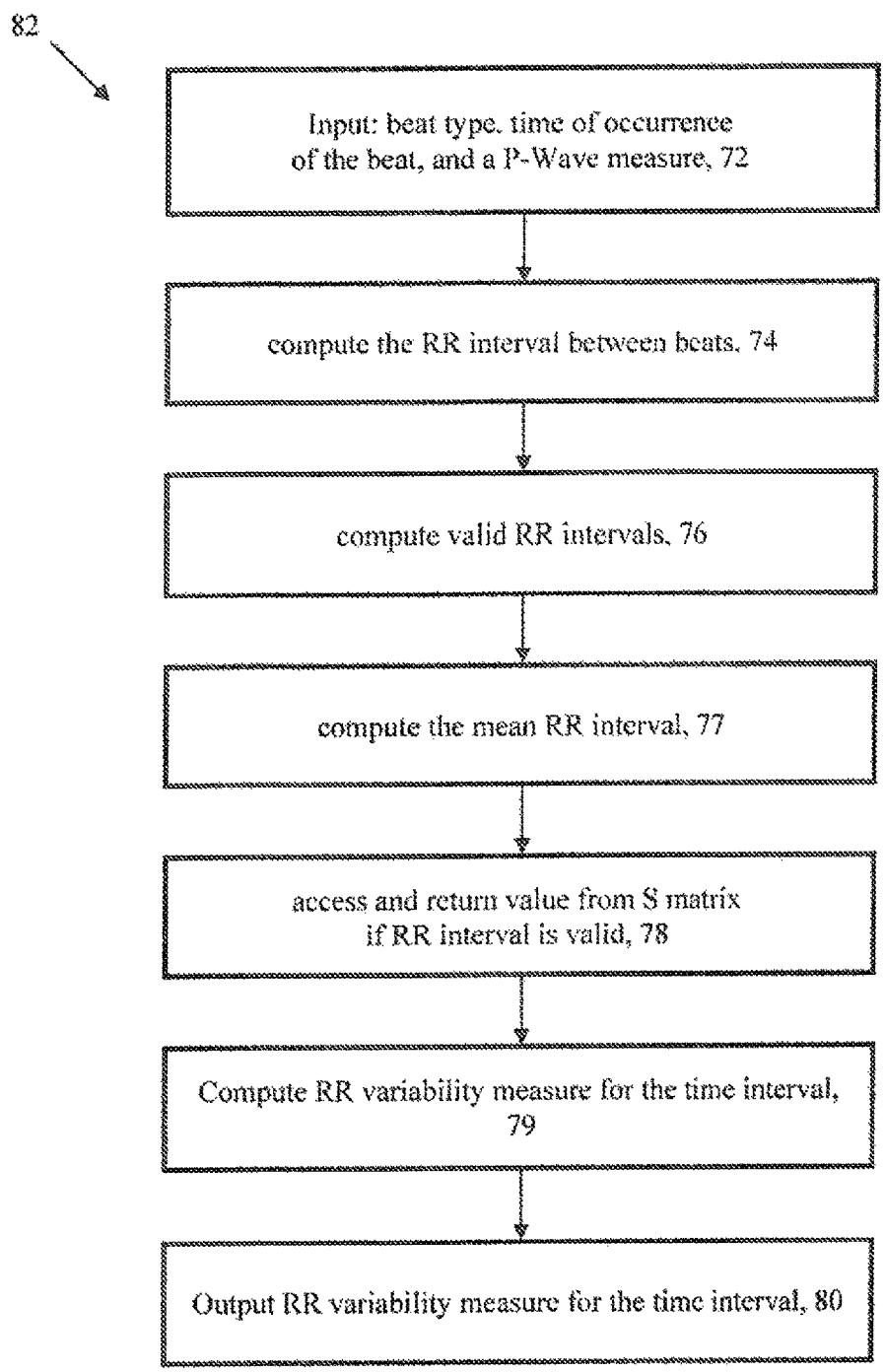

Referring to FIG. 6, an RR variability process 82 receives 72 as input beat type, time of occurrence of beat and a P-wave measure. The interval between beats is computed 74 as follows:

$$I[i]=T[i]-T[i-1]$$

A corresponding measure v[i] is used to determine 76 which RR intervals are "valid" with respect to determining AFib:

$$V[i] = \begin{cases} 1 & \text{if } (i > 0) \text{ and } (I[i] \leq 1.5 \text{ seconds}) \text{ and } B[i-1] \text{ and } B[i] \\ 0 & \text{otherwise} \end{cases}$$

The mean RR interval M[Z] is computed 77 recursively as follows:

$$M[i] = \begin{cases} 0.75M[i-1] + 0.25I[i] & \text{if } V[i] = 1 \\ M[i-1] & \text{otherwise} \end{cases}$$

A "coasting" process is used to copy the $i^{th}$ measure from the previous i−1 measure (e.g. M[i]=M[i−1]). The function L[i] classifies the RR intervals into one of three length classes (short, regular or long) using the mean. Thus, if v[i]=1

$$L[i] = \begin{cases} S: & \text{if } I[i] \leq 0.85M[i] \\ L: & \text{if } I[i] > 1.15M[i] \\ R: & \text{otherwise} \end{cases}$$

else $$L[i] = L[i-1]$$

In a paper by Moody, G., and Mark, G entitled: "A New Method for Detecting Atrial Fibrillation using R-R Intervals" Computers in Cardiology, p. 227-230 (1983) incorporated herein by reference, Moody et al produced a Markov Model of AFib using the MIT/BIH Arrhythmia database (Harvard University, Massachusetts Institute of Technology, Division of Health Sciences and Technology, Cambridge, Mass.).

Moody compiled statistics of transitions between the states {S,R,L}. The S matrix, below, describes the likelihood of AFib when transitioning from one RR interval to the next. The more negative the matrix element is, the more likely it is to be AFib.

for $j, k \in \{S, L, R\}$ $$S(j,k) = \begin{array}{c} \\ j = L[i] \end{array} \begin{array}{c} k = L[i-1] \\ \begin{array}{cccc} & S & R & L \\ S & -0.075 & -1.460 & 0.346 \\ R & -0.806 & 0.256 & -0.304 \\ L & 0.828 & -1.926 & 0.426 \end{array} \end{array}$$

The RR variability process 82 accesses 78 the S matrix if the beat intervals for S are "valid" for AFib, otherwise the likelihood of AFib is "coasted." The likelihood of AFib over the subwindow of two adjacent RR intervals is represented by F[i]:

If $i > 1$ $$F[i] = \begin{cases} S(L[i], L[i-1]) & \text{if } V[i] = 1 \text{ and } V[i-1] = 1 \\ F[i-1] & \text{otherwise} \end{cases}$$

else $$F[i] = S(R, R)$$

A boxcar filter is used for computing 79 the RR variability measure for the time window. The boxcar filter is a weighted average of the measures for each subwindow that takes into account the fraction of subwindow measures that were valid. The un-normalized, centered boxcar weight w[i] is defined as:

$$W[i] = \sum_{n=i-(N/2)}^{i+(N/2)-1} V[n]$$

where N=121. Note that V[n]=0 if n≤0 from the previous definition of V. Let R[i] represent the filtered 79 boxcar RR variability measure:

If $$W[i] > 0$$

then $$R[i] = \frac{\sum_{n=i-(N/2)}^{i+(N/2)-1} F[n]V[n]}{W[i]}$$

else $$R[i] = 0$$

Figure 7:
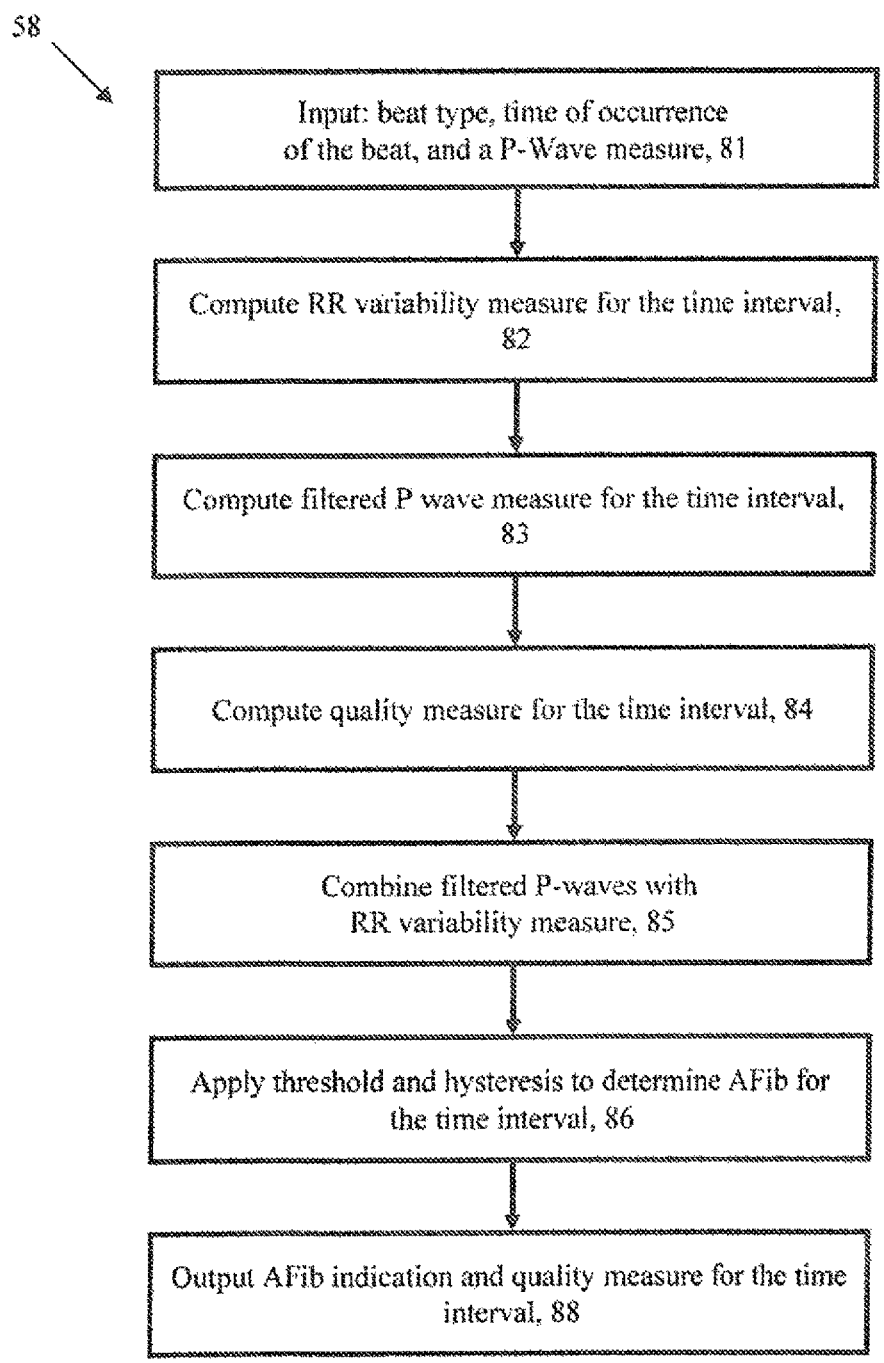

The RR variability measure determined above is output 80 to the AFib detector (FIG. 7).

Some variables need to be initialized if their equations refer to earlier values. Assuming the index i starts at 0:

I[0]=0

M[0]=I[0]

M[1]=I[1]

L[0]=R

Referring to FIG. 7, details of atrial fibrillation detector process 58 are shown. The atrial fibrillation detector 58 processes information representing events in a time window in the signal. One of the inputs, for example, represents information about the beats that occurred in the corresponding time window.

The atrial fibrillation detection process 58 combines, the RR variability measure, as discussed above, with an atrial activity measure (determined by the atrial process 57).

The atrial fibrillation detector process 58 receives inputs 81 as a time series of three measures for the $i^{th}$ beat detected in the signal: the beat type B[i], the time of occurrence of the beat T[i], and a P-Wave measure K[i]. The beat type B[i] indicates whether the $i^{th}$ beat originated in the atrium, and is otherwise normal (e.g., its beat interval does not contain a blocked P wave). The beat type B[i] is defined as:

$$B[i] = \begin{cases} \text{true} & \text{for beats of atrial origin whose previous interval does not contain a blocked } P \text{ wave} \\ \text{false} & \text{otherwise} \end{cases}$$

In practice, it is difficult to distinguish between atrial and nodal beats, so B[i] is taken to be true for all beats that are not of ventricular origin. B[i] is defined for all the possible types of beats in the control parameters defined below.

The time of occurrence of the beat T[i] is defined as:

T[i]=time of occurrence of the $i^{th}$ beat

The P-Wave measure K[i] measures P-Waves in RR intervals:

$$K[i] = \begin{cases} 1 & \text{if } (i > 0) \text{ and one } P\text{-Wave was detected between} \\ & T[i-1] \text{ and } T[i] \\ 0 & \text{otherwise} \end{cases}$$

The atrial fibrillation detector process 58 outputs 88, as discussed below, an AFib indication A[i] and a quality measure Q[i]:

$$A[i] = \begin{cases} \text{true} & \text{if } AFib \text{ in } RR \text{ interval } i \\ \text{false} & \text{otherwise} \end{cases}$$

$$Q[i] = \begin{cases} \text{true} & \text{if quality of } A[i] \text{ is above threshold} \\ \text{false} & \text{if quality of } A[i] \text{ is poor;} \\ & A[i] \text{ is being coasted} \end{cases}$$

The atrial fibrillation detector process 58 computes 82 an RR variability measure as was discussed in FIG. 6.

In a healthy heart, regular P-waves can be detected. During AFib, the number of detectable P-waves decreases. The AFib Detector process uses information about the number of P-waves in each RR interval. The AFib Detector process filters 83 the P-wave measure over the time window of 121 RR intervals. The presence or absence of P-waves is used in combination with RR variability to detect AFib.

The P-Wave boxcar filter 83 function P[i] is the same as the function for filtering RR variability (79 in FIG. 6), except that the P-Wave boxcar filter 83 function P[i] uses K[n] instead of F[n].

If $W[i] > 0$ then $$P[i] = \frac{\sum_{n=i-(N/2)}^{i+(N/2)-1} K[n]V[n]}{W[i]}$$

else $P[i] = 0$

The boxcar filter defines 84 a quality measure Z[i], for:

$$Z[i] = \frac{W[i]}{N}$$

Z[i] is the fraction of usable data in the time window, expressed as a value between zero and one, inclusive. A Boolean quality indicator is defined as:

$$Q[i] = \begin{cases} \text{true} & \text{if } Z[i] > q \\ \text{false} & \text{otherwise} \end{cases}$$

Quality Threshold:
q=0.65

P-waves, if they exist in the input stream, are used in combination 85 with the RR variability algorithm to detect AFib. Combining the presence or absence of P-waves with the RR variability measure augments the determination of AFib. A combined measure can take several forms. One example of a combined measure c[i] is determined as:

$$C[i] = \begin{cases} R[i] + p(P[i] - 0.5) & \text{if } Q[i] \text{ and } P[i] > r \\ R[i] & \text{otherwise} \end{cases}$$

Current values for constants:
P-Wave multiplier:
p=0.3

A P-Wave minimum threshold value is set at a specified minimum value, of e.g., r=0.05 (5%). The P-Wave minimum is used to eliminate the possibility of using P-Waves when no P-Waves are in fact detectable. A hysteresis value, h, is used in a filtered AFib determination 86, D[i].

$$D[i] = \begin{cases} C[i] < (s + h) & \text{if } D[i-1] = \text{true} \\ C[i] < s & \text{otherwise} \end{cases}$$

AFib threshold: s=−0.05, Hysteresis h=0.1

The process 58 outputs 88 the determined combined value A[i], as an indication of AFib. The final output 88 represents the filtered AFib indication for the $i^{th}$ RR interval. If the P wave quality is good and many P waves are detected, AFib is highly unlikely so the AFib indication is set to false. Otherwise, the AFib indication is "coasted" if quality is low:

If (Z[i] > 0.4) and (P[i] > 0.9)

then

A[i] = false else $$A[i] = \begin{cases} D[i] & \text{if } Q[i] \\ A[i-1] & \text{otherwise} \end{cases}$$

Some variables are initialized if their equations refer to earlier values. Assuming the index i starts at 0:
D[0]=false
A[0]=false Many of the parameters used in the AFib algorithm can be set to a default value. However, some of the parameters may be adjusted dynamically or according to patient parameters.

| Description | Name | Default Value |
|---|---|---|
| Max length of usable RR interval | (none) | 1.5 sec. |
| RR mean ratio | (none) | 25% |
| RR length percent | (none) | 15% |
| Number of boxcar elements | N | 121 RR intervals |
| P-Wave multiplier | p | 0.3 |
| Quality threshold | q | 65% |
| P-Wave minimum | r | 5% |
| AFib threshold | s | −5% |
| Hysteresis (used with s) | h | 0.1 |

Maximum RR Interval

When looking for RR variability, only regularly occurring beats are useful. When a detected RR interval is longer than a few seconds, the AFib algorithm ignores those RR intervals. This parameter controls the maximum usable RR interval.

RR Mean Ratio

This ratio is used in determining the mean RR interval.

RR Length Percent

This percentage is used in determining whether an RR interval is short, regular, or long.

Boxcar Size

The AFib detector filters the output over a time window of several RR intervals. This parameter determines how many RR intervals to use.

Quality Threshold (q)

Each RR interval is labeled as good or bad quality. This parameter determines when it is safe to use the output of any particular boxcar filter, depending on how many beats are good quality.

AFib Threshold (s)

The AFib Detector generates an analog AFib measure which is more negative as AFib is more likely. A threshold is used on this analog measure to create an output that is either on or off.

Hysteresis (h)

Hysteresis is used with the threshold to prevent the output from "bouncing" on and off right around the threshold point.

The monitor 10 and base station 20 can work cooperatively and collaboratively as a type of distributed processing system to strike a balance between the processing requirements on the monitor and the amount of data that is sent to the base station.

The Patient monitor 10 includes the functional components as shown in FIG. 1. Sensors are part of a front end that conditions and digitizes signals sensed from monitoring of a patient. The sensors may be conventional sensors, such as ECG electrodes or advanced technology, such as a garment that incorporate the sensors into the fabric. The sensors can alternatively be pressure transducers that measure pressure changes occasioned by blood flow.

Advantages include combining P waves and RR variability measurements in a manner that may be less error prone than other techniques. For example, a sequential process that uses the presence of P-waves, and if no P-waves or insufficient P waves are detected then uses RR interval information can be error prone because failure to detect even one P-wave can cause the detector to ignore all information about P-waves and rely solely on RR interval information. Since P-wave detection is difficult, especially in the presence of electrical noise on the ECG, such a sequential approach could be error prone and bias detection towards falsely declaring atrial fibrillation. On the other hand, if the sequential approach finds P-waves in all the beats, the sequential approach may ignore RR interval information.

In the techniques described above, P-wave and RR interval information are combined to produce a robust indication of atrial fibrillation. The techniques disclosed herein directly consider RR interval changes over a sequence of beats. These changes can be important in determining atrial fibrillation.

Figure 8:
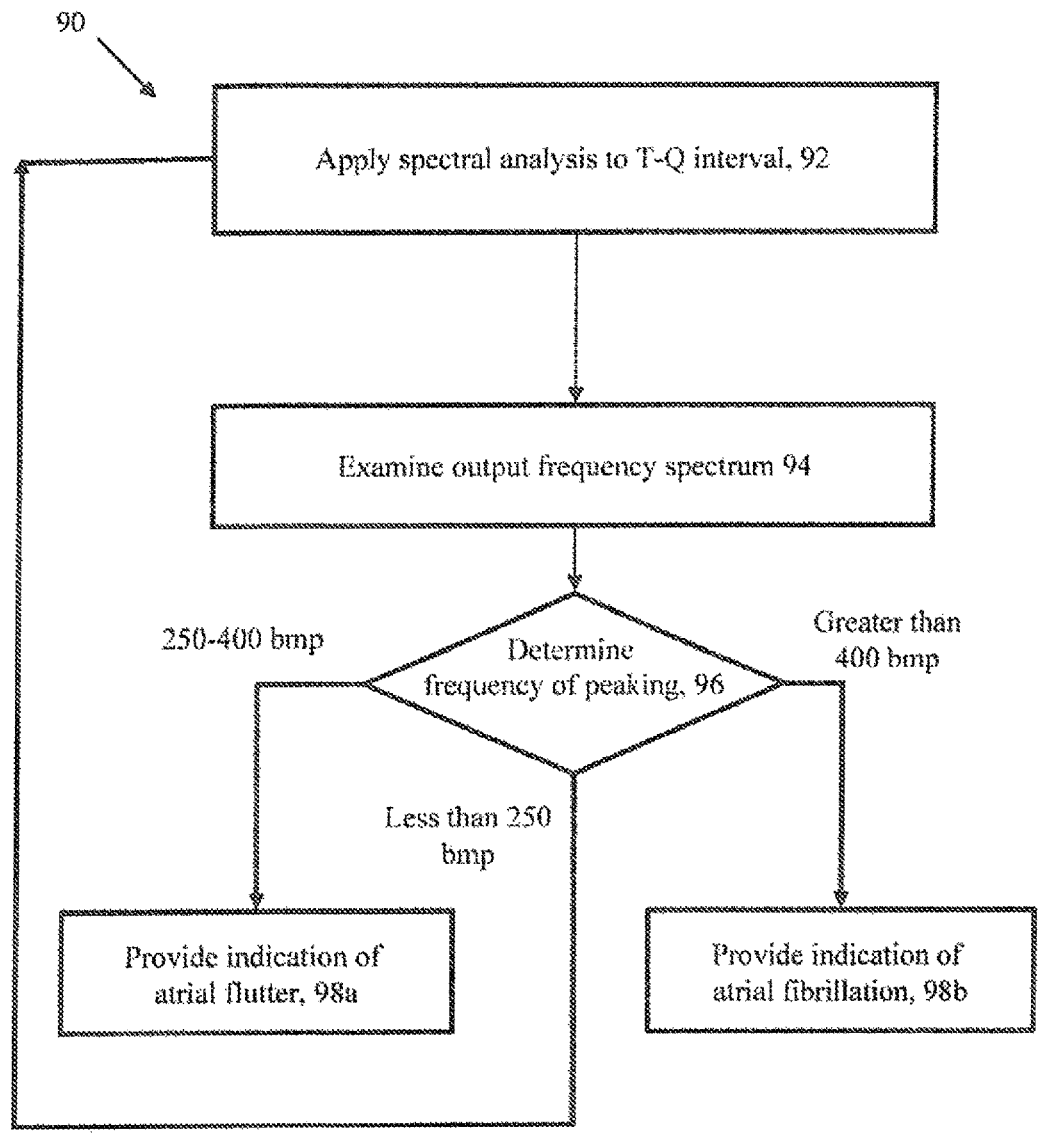

Referring to FIG. 8, a technique 90 that determines the presence of continuous cyclic atrial activity, which is associated with atrial flutter and coarse atrial fibrillation is shown. The approach applies 92 spectral analysis, such as applying the Fourier Transform, to the TQ interval of the ECG signal. Such spectral analysis will detect the continuous activity of flutter or coarse AFib. The process examines 94 an output frequency spectrum from the spectral analysis. The process 90 determines 96 frequencies corresponding to the presence of spectral peaking. If the frequencies that correspond to the repetitive activity are in the 250-400 beats per minute (BPM) range, which can be indicative of atrial flutter, the process can produce 98a an indication or an alert that indicates atrial flutter. If the frequencies that correspond to the repetitive activity are at a rate of near 400 BPM or higher, the process produces 98b an indication or an alert that indicates coarse atrial fibrillation. If the spectral peaking is at frequencies less than 250 no alert is produced.

Figure 9:
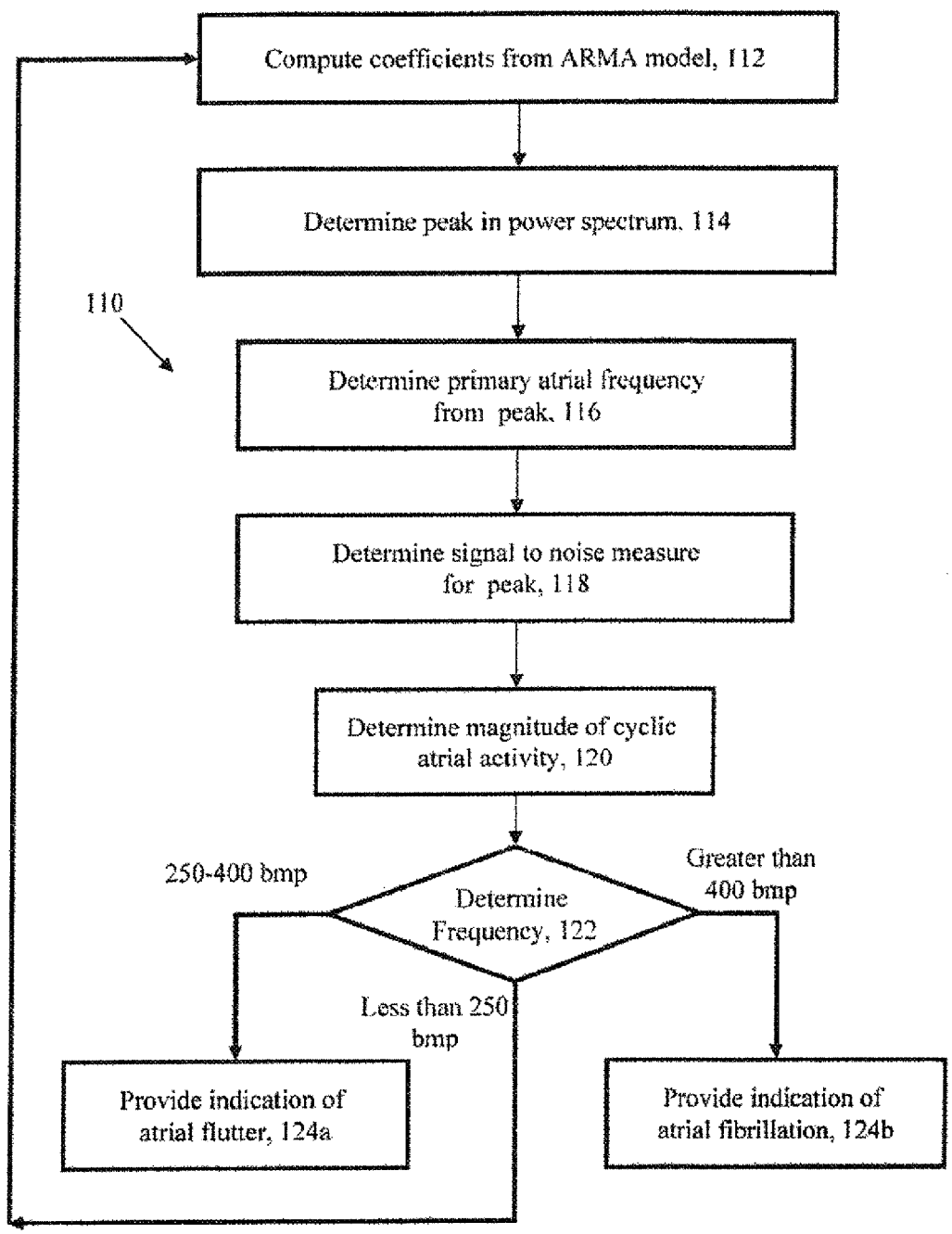

Referring to FIG. 9, continuous cyclic atrial activity can be characterized using a time-domain technique such as cross-correlation and autoregressive (AR) or autoregressive moving average (ARMA) model. For example, the coefficients of a $2^{nd}$ order ARMA model can be computed 112 from the ECG. The peak in the power spectrum of the ARMA model is determined 114. Then the atrial frequency corresponding to that peak is determined 116 to be the primary atrial frequency. The process 110 determines 118 the ratio of the power in the peak to the total power in the ARMA model, which is used as a signal-to-noise quality measure in assessing the detected peak. The total power represented in the ARMA model is determined 120 and used as a measure of the magnitude of the continuous cyclic atrial activity. If the peak's signal to noise quality is high, and the magnitude of the detected atrial activity surpassed a threshold, then the frequency of the peak is used to determine 122 an indication 124a of atrial flutter or an indication 124b of coarse atrial fibrillation (as in spectral analysis above).

Both the spectral measures and/or the time-domain models of atrial activity can also be used in combination with techniques to remove part or the entire QRST signal, which represents the electrical activity due to the ventricles. By removing the ventricular waveform corresponding to the activity of the ventricles, one can expose the residual signal and emphasize the atrial activity. The ability to measure atrial activity at more time points in the ECG, including those previously obscured by a ventricular waveform, allows an improved ability to detect patterns of atrial activity, such as P waves, atrial fibrillation activity, or atrial flutter waves.

The atrial activity detector works on one or more ECG channels. Each ECG channel is processed independently. The information from multiple adjacent RR intervals is filtered using the boxcar filter as described above. The filtered information from each channel is combined.

The boxcar filter described above can be replaced by other types of filters that improve the statistical reliability of the time interval measures.

Figure 10:
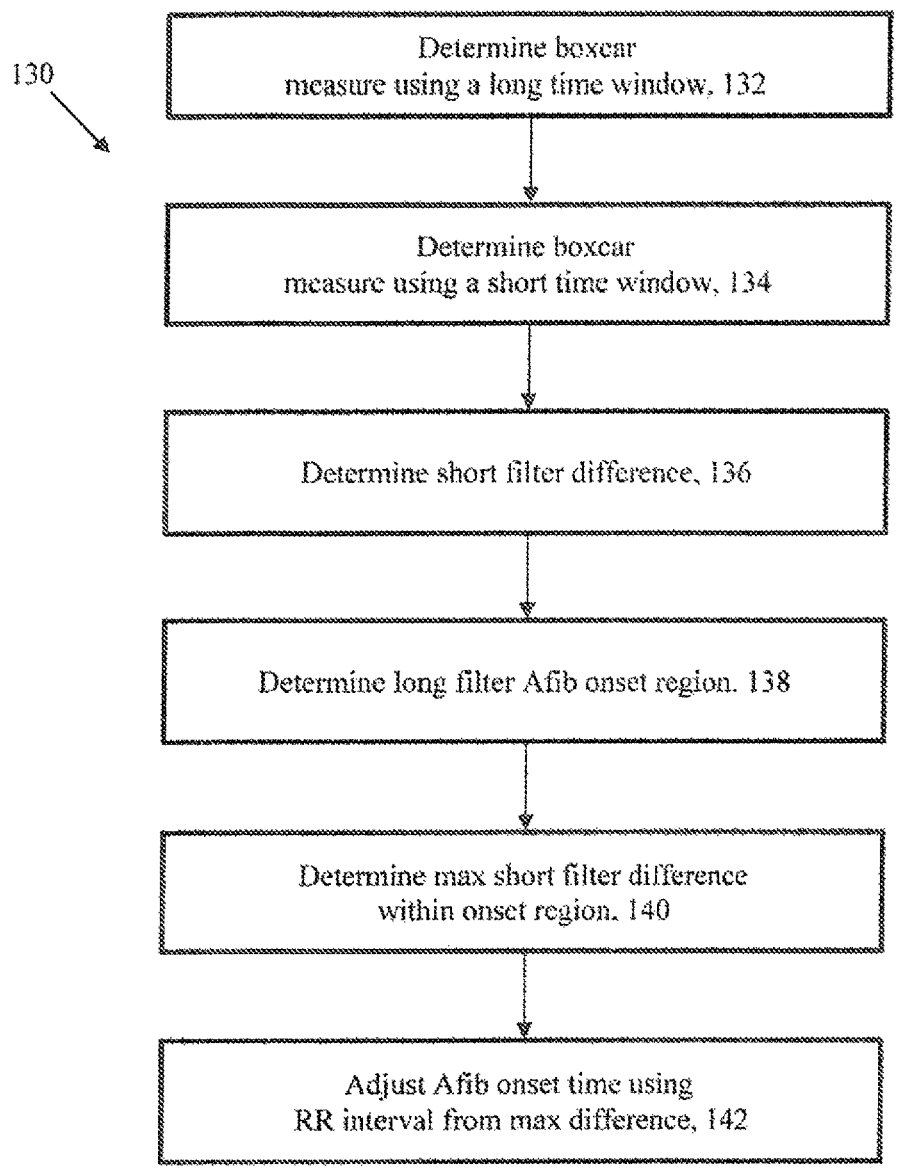

Referring to FIG. 10, the boxcar filter described above in FIG. 6 can be enhanced using a multi-filter technique 130, in order to improve the detection of short episodes of AFib and provide a more exact determination of the start and end of an AFib episode. The boxcar filter described above, in one example, uses a time window of, 121 beats for the RR variability measure. The multi-filter technique 130 uses 132 a filter with a long time window (e.g. 121 beats) and a short filter that operates 134 over a subwindow of the long time window (e.g. 5 beats). The results of the short boxcar filter are analyzed near the long filter's AFib onset time until the difference between 2 adjacent subwindows is maximized, as follows:

For each RR interval, the short filter difference is determined 136 by subtracting the output of the short filter of the RR intervals just previous to the RR interval from the output of the short filter of the RR intervals just past this RR interval. The long filter AFib onset region is determined 138 to be a region near the long filter AFib onset time (e.g. +/−30 RR intervals). Within the long filter AFib onset region, the process 130 determines 140 the maximum short filter difference. The adjusted AFib onset time is determined 142 to be the RR interval associated with the maximum short filter difference in the long filter AFib onset region. The same method is used similarly for AFib offset.

To detect short episodes of AFib (e.g. less than 30 seconds), a similar technique is used. The trigger threshold for the long boxcar is raised (e.g. from −0.05 to −0.10) and the maximal difference of adjacent short filters is taken around the point of long filter AFib detection. If the short filters detect a sufficient level of difference, then a short interval of AFib is indicated. If the short filters do not show enough of a difference, then no AFib episode is indicated.

An alternative method for measuring P wave conduction involves taking the standard deviation of a PR interval. When the standard deviation is low, consider the P to have conducted. The entire AFib detection algorithm can be enhanced by using the P wave conduction measure to rule out AFib, as follows. If enough P waves in the candidate AFib interval are conducting, then the interval represents some irregular rhythm other than AFib.

Other advantages include the use of multi-channel P wave detection and filtering of P waves over a time window, e.g., 60 beats, 120 beats, and so forth. The techniques use a Markov model for determining RR variability for atrial fibrillation detection and combine P waves and RR variability measurements to arrive at an indication of atrial fibrillation. The techniques can be adapted for both atrial fibrillation and atrial flutter detection. The techniques can be adapted to use the entire RR interval to look for P waves. Detection of blocked P waves is used as an input to prevent those RR intervals with blocked P waves from being used in the AFib algorithm.

A number of embodiments of the invention have been described. For example, the atrial activity measure detects atrial activity by detecting P waves. However, other types of atrial activity measures, such as the spectral analysis or ARMA techniques described above, could be used in addition to, or in lieu of, the P-wave measures. As another example, subwindows may be determined differently than those described above in the AFib likelihood determination 78 or the multi-filter method 130. Each subwindow may span an arbitrary number of beat intervals or an arbitrary amount of time. The subwindows may be overlapping or non-overlapping.

Thus, it will be understood that various modifications may be made without departing from the spirit and scope of the invention. Accordingly, other embodiments are within the scope of the following claims.

What is claimed is:

1. A method to detect atrial fibrillation, the method comprising:
   receiving an electrical signal representative of a beating heart;
   measuring atrial activity over a time window of three or more beats;
   measuring beat interval variation over the time window;
   performing time-domain processing on the electrical signal to determine the primary atrial frequency;
   combining the measures of atrial activity, beat interval variation, and primary atrial frequency to produce an indication of an atrial fibrillation condition in the electrical signal; and
   generating an alert based on the indication of an atrial fibrillation condition.

2. The method of claim 1 further comprising the step of: utilizing the electrical signal to create a reference template for beat classification.

3. The method of claim 1 further comprising the step of: utilizing the electrical signal to create a reference template for rhythm classification.

4. The method of claim 1 further comprising the step of: processing the atrial activity and beat interval variation using both a base station and a mobile device.

5. The method of claim 1 further comprising the step of: saving a cardiac event in a mobile device non-volatile memory.

6. The method of claim 1 further comprising the step of: uploading a cardiac event to a base station, wherein a base station is defined as a remote computer system.

7. The method of claim 1 further comprising the step of: providing periodic updates of measured atrial activity or beat interval variation to a base station.

8. The method of claim 1 further comprising the step of: utilizing a plurality of monitors to measure atrial activity or beat interval; and
   servicing the plurality of monitors with a single base station.

9. The method of claim 1 further comprising the step of: sending updated parameters from a base station to a monitor.

* * * * *